(12) United States Patent
Xu et al.

(10) Patent No.: US 7,713,542 B2
(45) Date of Patent: May 11, 2010

(54) THREE DIMENSIONAL CELL PROTECTOR/PORE ARCHITECTURE FORMATION FOR BONE AND TISSUE CONSTRUCTS

(75) Inventors: Huakun Xu, Frederick, MD (US); Michael D. Weir, Silver Spring, MD (US)

(73) Assignee: ADA Foundation, Chicago, IL (US)

( * ) Notice: Subject to any disclaimer, the term of this patent is extended or adjusted under 35 U.S.C. 154(b) by 295 days.

(21) Appl. No.: 11/132,028

(22) Filed: May 18, 2005

(65) Prior Publication Data

US 2006/0159717 A1 Jul. 20, 2006

Related U.S. Application Data

(60) Provisional application No. 60/644,421, filed on Jan. 14, 2005.

(51) Int. Cl.
*A61F 2/02* (2006.01)
(52) U.S. Cl. .................. 424/426; 424/422; 424/484; 424/93.7; 623/16.11; 623/23.56; 623/23.61; 623/23.62
(58) Field of Classification Search ................. None
See application file for complete search history.

(56) References Cited

U.S. PATENT DOCUMENTS

| | | | |
|---|---|---|---|
| 4,353,888 A | 10/1982 | Sefton | |
| 4,892,538 A | 1/1990 | Aebischer et al. | |
| 5,525,148 A | 6/1996 | Chow et al. | |
| 5,545,254 A | 8/1996 | Chow et al. | |
| 5,976,234 A | 11/1999 | Chow et al. | |
| 5,997,624 A | 12/1999 | Chow et al. | |
| 6,132,463 A | 10/2000 | Lee et al. | |
| 6,139,578 A | 10/2000 | Lee et al. | |
| 6,143,293 A | 11/2000 | Weiss et al. | |
| 6,277,151 B1 | 8/2001 | Lee et al. | |
| 6,544,290 B1 | 4/2003 | Lee et al. | |
| 2002/0055143 A1 | 5/2002 | Bell et al. | |
| 2003/0019396 A1 | 1/2003 | Edwards et al. | |
| 2003/0099630 A1 | 5/2003 | DiBenedetto et al. | |
| 2003/0206937 A1 | 11/2003 | Gertzman et al. | |
| 2004/0062809 A1 | 4/2004 | Honiger et al. | |
| 2004/0101518 A1 | 5/2004 | Vacanti et al. | |
| 2004/0131678 A1 | 7/2004 | Berger | |
| 2004/0137032 A1* | 7/2004 | Wang ................. | 424/423 |

OTHER PUBLICATIONS

Simon, Jr. et al "Preliminary report on the biocompatibility of a moldable, resorbable, composite bone graft consisting of calcium phosphate ement and poly(lactide-co-glycolide) microspheres" Journal of Orthopaedic Research, 2002, vol. 20, No. 3, pp. 473-482.*
Weng et al, "Tissue Engineered Composites of Bone and Cartilage for Mandible Condylar Reconstruction" Journal of Oral and Maxillofacial Surgery, 2001, vol. 59, pp. 185-190.*

Zaikov et al, "Biodegradable Polymers for Medicinal Use (Review)" Pharmaceutical Chemistry Journal, 1984, vol. 18, No. 4, pp. 235-244.*
Brown et al., *A New Calcium Phosphate, Water-Setting Cement*, American Ceramic Society (1986) pp. 352-379.
Damien et al., *Bone Graft and Bone Graft Substitutes: A Review of Current Technology and Applications*, Journal of Applied Biomaterials (1991) pp. 187-208, vol. 2.
O'Kelly et al., *A Quantitative Technique for Comparing Synthetic Porous Hydroxyapatite Structures and Cancellous Bone*, Journal of Materials Science: Materials in Medicine (1996) pp. 207-213, vol. 7.
Broz et al., *Effects of Deproteinization and Ashing on Site-Specific Properties of Cortical Bone*, Journal of Materials Science: Materials in Medicine (1997) pp. 395-401, vol. 8.
Ginebra et al., *Setting Reaction and Hardening of an Apatitic Calcium Phosphate Cement*, J. Dent Res (Apr. 1997) pp. 905-912, vol. 76(4).
Constantz et al., *Histological, Chemical, and Crystallographic Analysis of Four Calcium Phosphate Cements in Different Rabbit Osseous Sites*, Calcium Phosphate Cements (1998) pp. 451-461.
Miyamoto et al., *Histological and Compositional Evaluations of Three Types of Calcium Phosphate Cements when Implanted in Subcutaneous Tissue Immediately After Mixing*, Three CPCs in Soft Tissue, (1999) pp. 36-42.
Tofighi et al., *A Biomimetic Bone Substitute and Drug Delivery Vehicle*, Clincial Orthopaedics and Related Research (1999) pp. 396-404, vol. 367.
Chow, *Calcium Phosphate Cements: Chemistry, Properties and Applications*, Mat. Res. Soc. Symp. Proc. (2000) pp. 27-37, vol. 599.
Von Gonten et al., *Load-Bearing Behavior of a Simulated Craniofacial Structure Fabricated from a Hydroxyapatite Cement and Bioresorbable Fiber-Mesh*, Journal of Materials Science: Materials in Medicine (2000) pp. 95-100, vol. 11.
Matsuya, *Effect of Mixing Ratio and pH on the Reaction Between $Ca_4(PO_4)_2O$ and $CaHPO_4$*, Journal of Materials Science: Materials in Medicine (2000) pp. 305-311, vol. 11.
Takagi et al., *Morphological and Phase Characterizations of Retrieved Calcium Phosphate Cement Implants*, Characterizations of Retrieved Calcium Phosphate Cement Implants (2000) pp. 36-41.
Xu et al., *Reinforcement of a Self-Setting Calcium Phosphate Cement with Different Fibers*, Reinforcement of Calcium Phosphate Cement with Fibers (Oct. 2000) pp. 107-114.
Lee et al., *Degradable and Injectable Poly(aldehyde guluronate) Hydrogels for Bone Tissue Engineering*, Degradable and Injectable Hydrogels (2001) pp. 228-233.
Lucksanasombool et al., *Fracture Toughness of Bovine Bone: Influence of Orientation and Storage Media*, Biomaterials (2001) pp. 3127-3132, vol. 22.
Takagi et al., *Formation of Macropores in Calcium Phosphate Cement Implants*, Journal of Materials Science: Materials in Medicine (2001) pp. 135-139, vol. 12.

(Continued)

*Primary Examiner*—Allison M Ford
(74) *Attorney, Agent, or Firm*—Banner & Witcoff, Ltd.

(57) ABSTRACT

Living cellular material is encapsulated or placed in a protective material (cell protector) which is biocompatible, biodegradable and has a three-dimensional form. The three dimensional form is incorporated into a matrix that maybe implanted in vivo, ultimately degrade and thereby by replaced by living cell generated material.

15 Claims, 8 Drawing Sheets

OTHER PUBLICATIONS

Xu et al., *Strong and Macroporous Calcium Phosphate Cement: Effects or Porosity and Fiber Reinforcement on Mechanical Properties*, Macroporous Calcium Phosphate Cement (2001) pp. 457-466.

Simon Jr. et al., *Preliminary Report on the Biocompatibility of a Moldable, Resorbable, Composite Bone Graft Consisting of Calcium Phosphate Cement and Poly(lactide-co-glyycolide) Micropheres*, Journal of Orthopedic Research (2001) pp. 1-10.

Xu et al., *Calcium Phosphate Cement Containing Resorbable Fibers for Short-Term Reinforcement and Macroporosity*, Biomaterials (2002) pp. 193-202, vol. 23.

Xu et al., *Synergistic Reinforcement of In Situ Hardening Calcium Phosphate Composite Scaffold for Bone Tissue Engineering*, Biomaterials (2004) pp. 1029-1037, vol. 25.

Xu et al., *Fast Setting Calcium Phosphate Scaffolds with Tailored Macropore Formation Rates for Bone Regeneration*, Calcium Phosphate Scaffolds for Bone Regeneration (2004) pp. 725-734.

Xu et al., *Self-Hardening Calcium Phosphate Composite Scaffold for Bone Tissue Engineering*, Journal of Orthopaedic Research (2004) pp. 535-543, vol. 22.

Xu et al., *Self-Hardening Calcium Phosphate Cement-Mesh Composite: Reinforcement, Macropores, and Cell Response*, Journal of Biomedical Materials Research—Part A (2004) pp. 267-278.

Drury et al., *The Tensile Properties of Alginate Hydrogels*, Biomaterials (2004) pp. 3187-3199, vol. 25.

Simon Jr. et al., *Cell Seeding Into Calcium Phosphate Cement*, Cell Seeding into Calcium Phosphate Cement (2004) pp. 628-639.

Xu et al., *Fast Setting Calcium Phosphate-Chitosan Scaffold: Mechanical Properties and Biocompatibility*, Biomaterials (2005) pp. 1337-1348, vol. 26.

International Search Report, International Application No. PCT/US06/00955, Mailing date Jun. 5, 2008.

Notification of Transmittal of the International Search Report and the Written Opinion of the International Search Authority, or the Declaration for International Application No. PCT/US06/00955, dated Jun. 5, 2008.

International Preliminary Report on Patentability, International Application No. PCT/US06/000955, Mailing date Mar. 12, 2009.

* cited by examiner

THREE DIMENSIONAL CELL PROTECTOR/PORE ARCHITECTURE FORMATION FOR BONE AND TISSUE CONSTRUCTS

STATEMENT REGARDING FEDERALLY SPONSORED RESEARCH OR DEVELOPMENT

The subject matter of this invention was supported, at least in part, by grants from the National Institutes of Health, NIDCR grant R01 DE 14190 thereby resulting in potential use and/or license rights in the U.S. government and/or other entities pursuant to grant terms.

CROSS-REFERENCE TO RELATED APPLICATION

This is a utility application derived from and based upon Ser. No. 60/644,421 filed Jan. 14, 2005 entitled Three Dimensional Cell Protector/Pore Architecture Formation for Bone and Tissue Constructs incorporated herewith by reference and for which priority is claimed.

BACKGROUND OF THE INVENTION

In a principal aspect, the present invention relates to a construct for protecting biologics (such as cellular materials, particularly living cellular materials) by use of three-dimensional protective structures for such biologics using generally non-reactive, three dimensional containment materials so as to enable use of such combinations in vivo and in vitro environments for growth and/or replacement of damaged or missing cellular structure such as bone.

The need for biomaterials has increased as the world population ages. Due to its chemical and crystallographic similarity to the carbonated apatite in human bones, hydroxyapatite has found applications. While sintered hydroxyapatite needs machining and is used in prefabricated forms, calcium phosphate cements can be molded as pastes and set in situ (Brown and Chow, A new calcium phosphate water setting cement, pp. 352-379 in Brown, Cements research progress, American Ceramic Society, OH, 1986; Ginebra et al., Setting reaction and hardening of an apatite calcium phosphate cement, J. Dent. Res. 76:905-912, 1997; Constantz et al., Histological, chemical, and crystallographic analysis of four calcium phosphate cements in different rabbit osseous sites, *J. Biomed. Mater. Res. [Appl. Biomater].* 43:451-461, 1998; Miyamoto et al., Histological and compositional evaluations of three types of calcium phosphate cements when implanted in subcutaneous tissue immediately after mixing, *J. Biomed. Mater. Res. [Appl. Biomater.]* 48:36-42, 1999; Lee et al., Alpha-BSM(R): A biomimetic bone substitute and drug delivery vehicle, *Clin. Orthop Rel. Res.* 367:396-405, 1999). Calcium phosphate cement, referred to as CPC, is comprised. of a mixture of fine particles of tetracalcium phosphate [TTCP: $Ca_4(PO_4)_2O$] and dicalcium phosphate anhydrous [DCPA: $CaHPO_4$]. The CPC powder can be mixed with water to form a paste that can intimately conform to osseous defects with complex shapes and set in vivo to form a hydroxyapatite-containing implant. Due to its in-situ setting ability, excellent osteoconductivity and bone replacement capability, CPC is promising for a wide range of clinical applications.

The term "in-situ setting" or "self-hardening" or "moldable" refers to the paste being able to set or harden inside a bone cavity or in a mold and being able to be shaped or contoured; for example, the CPC paste can be placed into a bone cavity and harden when in contact with an aqueous medium (Matsuya et al., Effects of mixing ratio and pH on the reaction between $Ca_4[PO_4]_2O$ and $CaHPO_4$, *J. Mater. Sci.: Mater. in Med.* 11:305-311, 2000; Takagi et al., Morphological and phase characterizations of retrieved calcium phosphate cement implants, *J. Biomed. Mater. Res. [Appl. Biomater.]* 58:36-41, 2001). U.S. Pat. Nos. 5,525,148, 5,545,254, 5,976,234, and 5,997,624 (Chow et al.) disclose methods for calcium phosphate cements including fillers and pore forming agents. Xu et al. suggest fiber reinforcement of calcium phosphate cement in "Reinforcement of a self-setting calcium phosphate cement with different fibers", *J. Biomed. Mater. Res.* 52:107-114 (2000) and in "Effects of fiber length and volume fraction on the reinforcement of calcium phosphate cement", *J. Mater. Sci.: Mater. in Med.* 12:57-65 (2001). Von Gonten et al. suggest a single sheet of mesh reinforcement for calcium phosphate cement in "Load-bearing behavior of a simulated craniofacial structure fabricated from a hydroxyapatite cement and bioresorbable fiber-mesh", *J. Mater. Sci.: Mater. in Med.* 11:95-100 (2000). However, in these studies, there has been no mention of incorporating living cells into CPC. Takagi et al. suggest the formation of macropores resulting from the dissolution of soluble fillers or pore forming agents in "Formation of macropores in calcium phosphate cement implants", *J. Mater. Sci. Mater. in Med.* 12:135-139 (2001). Chow reviews calcium phosphate cements in "Calcium phosphate cements: Chemistry, properties, and applications", *Mat. Res. Symp. Proc.* 599:27-37 (2000). Xu et al. incorporate fibers and pore forming agents in "Strong and macroporous calcium phosphate cement: Effects of porosity and fiber reinforcement on mechanical properties", *J. Biomed. Mater. Res.* 57:457466 (2001). Xu et al. use resorbable fibers in "Calcium phosphate cement containing resorbable fibers for short-term reinforcement and macroporosity", *Biomaterials* 23:193-202 (2002). Xu et al. use synergistic reinforcement to develop scaffolds in "Effects of Synergistic reinforcement on in situ hardening calcium phosphate composite scaffold for bone tissue engineering" *Biomaterials* 25:1029-1037 (2004). Xu et al. also develop fast-setting and anti-washout CPC in "Fast-setting and anti-washout calcium phosphate scaffolds with high strength and controlled macropore formation rates", *Journal of Biomedical Materials Research* 68A:725-734 (2004). However, in these studies there is no mention of mixing living cells into the CPC paste.

Cell culture studies were performed on CPC to investigate the biocompatibility of CPC (Simon et al., Preliminary report on the biocompatibility of a moldable, resorbable, composite bone graft consisting of calcium phosphate cement and poly [lactide-co-glycolide] microspheres. *J Orthop Res* 20:473-482, 2002). Cell culture was performed to investigate the biocompatibility of CPC-fiber composite by using osteoblast-like cells (Xu et al., Self-hardening calcium phosphate composite scaffold for bone tissue engineering. *Journal of Orthopaedic Research* 22:535-543, 2004), CPC-mesh composite (Xu et al., Self-hardening calcium phosphate cement-mesh composite: Reinforcement, macropores, and cell response. *Journal of Biomedical Materials Research* 69A: 267-278, 2004), and fast-setting CPC composite (Xu et al., Fast-setting calcium phosphate-chitosan scaffold: Mechanical properties and biocompatibility, Biomaterials, in review, 2004). Cells were seeded onto the specimens surfaces. The cell attachment, live and dead cell staining, and cell viability were investigated for these compositions. However, in these studies, no cells were mixed into the CPC paste. The CPC specimens were set or hardened without any cells in them. The cells were subsequently attached to the surfaces of the already hardened specimens.

U.S. Pat. No. 4,353,888 (Sefton) discloses encapsulation of viable mammalian cells to form beads for introduction into a host body. U.S. Pat. No. 4,892,538 (Aebischer et al.) discloses in vivo delivery of neurotransmitters by implanted, encapsulated cells using a semipermeable membrane which permits the diffusion of the neurotransmitter while excluding viruses and antibodies. U.S. Pat. No. 6,132,463 (Lee et al.), U.S. Pat. No. 6,139,578 (Lee et al.), U.S. Pat. No. 6,277,151 (Lee et al.), and U.S. Pat. No. 6,544,290 (Lee et al.) disclose a poorly-crystalline apatitic calcium phosphate material seeded with cells for bone and cartilage growth, in vitro cell culture systems and cell encapsulation matrices. U.S. Pat. No. 6,143,293 (Weiss et al.) discloses in-direct pre-formed scaffolds that can be seeded with cells: U.S. Pat. Application 2004/0101960 A 1 (Schaefer et al.) discloses an injectable hydroxyapatite cement containing living cells as a bone substitute material. Simon et al. (Cell seeding into calcium phosphate cement, *Journal of Biomedical Materials Research*, 68; A:628-639, 2004) show cell encapsulation in alginate beads that are then mixed with a CPC paste. None of this prior art mentions the design of three-dimensional cell protectors of lattice-like structures, or zigzag or woven or curved structures, or three-dimensional web-like structures. Furthermore, none of this prior art mentions the development of cell protectors for two functions: (1) protecting the cells from the surrounding environment for a predetermined time period; (2) controlled formation of three-dimensional pore architectures when the cell protectors dissolve and concomitantly release the living cells into the highly-interconnected pore structures in the in-situ setting implant.

U.S. Pat. Application 2002/0055143 A1 (Bell et al.) discloses bone precursor compositions including an injectable calcium cement than can be conditioned with cells, preferably bone tissue cells. It does not mention the use of three-dimensional cell protectors/pore architecture builders. U.S. Pat. Application 2003/0019396 A 1 (Edwards et al.) discloses a porous cement which self sets to hydroxyapatite and has an interconnected porosity. It does not mention the mixing of cells into the cement paste. U.S. Pat. Application A1 2003/0099630 (DiBenedetto et al.) discloses a bioactive material using fibroin solutions and suspensions that is injectable and able to form pores, and can release compounds in a controlled manner to enhance growth and activation of cells. It does not mention the mixing of cells into the injectable composition and the use of cell protectors/pore architecture builders.

U.S. Pat. Application 2003/0206937 A 1 (Gertzman et al.) discloses a malleable bone putty including a bone powder mixed in a hydrogel carrier. U.S. Pat. Application 2004/0062809 A1 (Honiger et al.) discloses porous biocompatible polymers in the form of hydrogels with a three-dimensional structure and communicating cells. Its three-dimensional structure refers to the structure of the porous implant as a whole; it does not refer to the formation of the pores alone. It does not mention the use of cell protectors/pore architecture builders incorporated inside an in situ implant matrix material.

U.S. Pat. Application 2004/0101518 A1 (Vacanti et al.) discloses a hydrogel-cell composition with a support structure having a predetermined shape that corresponds to the shape of a desired tissue. It does not use the hydrogel to protect the cells and form pore structures in the final implant. Neither does it mention the use of cell protectors and pore architecture builders that are incorporated inside an in situ implant matrix material.

U.S. Pat. Application 2004/0131678 A1 (Burger et al.) discloses a water based bone cement comprising a slow release bone growth factor and a fast release antimicrobial agent. U.S. Pat. Application 2004/0137032 A1 (Wang) discloses combinations of calcium phosphates, bone growth factors, and pore-forming additives as osteoconductive and osteoinductive composite bone grafts. It relates to the degradation of polymer microspheres as porogens leading to macropores that facilitate the growth of osteoblasts into the bone grafts. The cells are grown into the pores of the graft after the paste setting; the cells are not mixed into the paste prior to the paste setting. In this application the cells attach to a set and hardened surface. Furthermore, the polymer microspheres and/or water-soluble particles create pores that are sphere-like, discrete, or particle-shaped. It does not mention the use of cell protectors of three-dimensional lattice-like structures, or zigzag or woven or curved structures, or three-dimensional web-like structures. Nor does it mention the three-dimensional pore architecture builders where the cells are incorporated throughout the entire interior of the implant prior to the paste setting.

In conclusion, in prior art, there has been no mention of methods of fabricating surgical moldable and self-hardening implants containing living cells prior to paste placement where said living cells are protected in three-dimensional cell protectors for a prescribed time period, said protectors then subsequently dissolve at a predetermined time to free the cells inside the implant and concomitantly form three-dimensional pore architectures as cell and nutrient passageways throughout the entire interior of the implant.

Furthermore, there has been no mention in prior art of the design of cell protectors/pore architecture builders of three-dimensional lattice-like structures, zigzag or woven or curved structures, or three-dimensional web-like structures inside surgically placed implants. These structures serve two important functions: (1) protecting the cells, for a controlled period of time, from any undesirable environment including mechanical damage, pH changes, ion activities, and excessive temperature changes during paste setting; and (2) at a prescribed time, creating engineered three-dimensional pore architectures as cell nutrient and communication passageways throughout the implant.

In addition, in prior art, there has been no mention of using three-dimensional cell protectors/pore architecture builders inside a surgical moldable and self-hardening implant, with three-dimensional cell protectors/pore architecture builders having designed sizes, effective diameters, interconnectivity sizes, and degradation rates matching the applications, so that the cells can be released and pores created at a controlled time or at graded times.

SUMMARY OF THE INVENTION

A new technology has been discovered for developing moldable and self-hardening implant compositions comprising living cells situated inside protectors useful for medical, veterinary, dental, periodontal, craniofacial, and orthopedic repairs. The implant materials containing living cells in the protectors described may be available in the form of a paste for injection delivery and intimate fitting to the tissue cavity, overcome three major challenges: (1) difficulty in getting the living cells deep into a scaffold instead of cells only attaching to the surface of the implant; (2) difficulty in building highly-interconnected pore architectures in the implant body with living cells filling these pores; (3) difficulty in protecting the living cells for a critical period of time prior to implant formation or hardening or placement, followed by quick release of the cells to avoid cell death and to initiate cellular function and new tissue growth.

Thus this invention relates to methods and compositions of three-dimensional cell protectors inside a moldable and self-hardening implant thereby protecting living cells from any undesirable environment such as pH changes, ion activities and mechanical disruption during implant manipulation and placement. Disclosed cell protectors typically have unique structures including three-dimensional lattice-like structures with cells living inside them, zigzag or woven or curved structures, or three-dimensional web-like structures. After fulfilling their first function, these protectors dissolve away. Thus, they initially build or rest in highly-interconnected three-dimensional pore architectures, at a prescribed time (for example, after implant setting), to serve as cell activity passageways throughout the entire implant. The cell protectors/pore architecture builders possess designed sizes, diameters, interconnectivity, and controlled degradation rates matching their applications, so that the cells can be released at a predetermined time to migrate, interact, and secrete new bone and tissues inside and throughout the entire implant. Such protector degradation rates can be controlled from a few minutes to several weeks as needed. It further allows different cells [bone-growing cells (osteoblasts), blood vessel-growing cells (endothelial cells), cartilage growing cells (chondrocytes), implant-degrading and resorbing cells (osteoclasts), etc.] to be released at controlled times in tailored parts or layers of the implant.

One purpose of this invention is to develop improved tissue regenerating constructs useful for dental, periodontal, craniofacial, orthopedic and other tissue regeneration repairs. Thus living cells can be obtained from the same patient destined to receive an implant and can be greatly multiplied in vitro. Then when being placed into a surgical repair, the living cells are stored in engineered cell protectors embedded in a surgical self-hardening matrix material for a prescribed period of time so that the cells are not harmed by events such as matrix manipulation, the chemistry of the matrix environment or setting reactions. The protectors can be in the shapes of long tubes or rods or three-dimensional lattice-like structures. Once the surgical matrix material is manipulated into the surgical site and it is no longer harmful to the cells, the three-dimensional cell protectors dissolve, thereby freeing and releasing the cells inside and throughout the implant. Concomitantly, the dissolution of the protectors form three-dimensional rod-shaped pore architectures that are highly-interconnected throughout the interior of the implant. Therefore, the cells can migrate, interact and attach throughout the interior of the implant and form new bone or other tissues throughout the implant. Since the matrix is resorbable, new tissue can form and eventually there is no presence of a foreign implant or residual implant material remaining.

Hence, the overall purpose is to develop an in-situ cell protecting and self-hardening implant material:

1. That is capable of containing and maintaining living cells prior to the implant formation and placement. This is advantageous because the cells are distributed throughout the entire self-hardening implant and are protected from mechanical and chemical damage during paste mixing, manipulation and setting of the implant matrix material, such as a moldable and self-hardening calcium phosphate bone cement. Other methods that seed cells only after the implant is formed or hardened only have cells on the surface or in a shallow surface layer. Methods that directly mix cells into the implant materials risk cell damage or death due to mechanical, thermal and chemical damages.

2. That has engineered three-dimensional lattice-like structures, zigzag or woven or curved structures, or three-dimensional web-like structures that can build three-dimensional pore architectures, thus allowing critically-important cell migration, interactions and nutrient access throughout the implant.

3. That has a controlled degradation rate for the cell protectors to match specific requirements, for example, to match the different setting times of various implant cements. Within or during a generally predetermined time period the cells are protected inside the protectors. After that, the protectors dissolve and the cells are promptly released and three-dimensional pore architectures simultaneously created in the implant. This also allows different cells, for example, bone-growing cells (osteoblasts), blood vessel-growing cells (endothelial cells), cartilage growing cells (chondrocytes), implant-degrading and resorbing cells (osteoclasts), to be released at different controlled times in tailored parts or layers of the implant. It also provides the versatility to be applied to a variety of implant materials with widely differing compositions, working and setting times.

4. That yields a moldable and self-hardening implant, with living cells and engineered three-dimensional pore architecture inside, to possess mechanical strength, elastic modulus (stiffness), and work-of-fracture (toughness) that biomimetically match the values for natural tissues. This differs from previous approaches in that previous implant materials do not have living cells inside them prior to paste hardening. Further, the cell protector of this invention either provides reinforcement or modifies the implant physical properties to match the properties of the replacement natural tissue biomimetically.

In summary, the invention generally comprises:

1. Cell protectors of engineered three-dimensional, generally lattice-like structures with cells living inside them and comprise zigzag or woven or curved structures, or three-dimensional web-like structures that can protect the cells from mechanical and chemical damages. Then, at a prescribed time, the protectors dissolve and build or thereby provide three-dimensional pore architectures, said pore architectures being filled with cells throughout the in-situ hardening implant;

2. Has controlled degradation rate for the cell protectors to match specific requirements, for example, to match the different setting times of various bone cements, within which the cells are protected and after which the cells are promptly released and pore architectures simultaneously created; and allows different cells (bone-growing cells, blood vessel-growing cells, or implant-degrading cells) to be released at controlled times in the tailored parts or layers of the in-situ hardening implant; and 3. Self-hardening materials possessing mechanical strength, elastic modulus and work-of-fracture values that biomimetically match the mechanical property values for natural tissues.

BRIEF DESCRIPTION OF THE DRAWING

In the detailed description which follows, reference will be made to the drawing comprised of the following figures:

FIG. 2(a) is an example of cell protectors containing living cells inside. The cells are osteoblasts. The cell protectors are made of biocompatible and degradable polymers. Each rod or tube protector has a diameter of approximately 0.5 mm. There are approximately 580 cells inside each rod. Cell density can be adjusted according to specific applications. FIG. 2(B): The cell protector rods can be placed in the CPC paste to protect the cells during CPC manipulation and setting, and then dissolve to build cylindrical pores or tubes, ideal for cell migration deep in the implant. FIG. 2(C): Interconnected structure of cell protectors form web-like or three-dimensional lattice-like structures. Such structures in the CPC paste protect the cells. After CPC setting, the protector structure is dissolved, thus building a three-dimensional highly-interconnected pore structure filled with living cells throughout the porous CPC. FIG. 2(D): A higher magnification of FIG. 2(C).

FIG. 3(A): Cells in protectors are immersed in a cell culture medium (control); FIG. 3(B): Cells in protectors are immersed in a freshly-mixed CPC paste; FIG. 3(C): Cells in protectors are immersed in a freshly-mixed CPC-chitosan paste; and FIG. 3(D) cells in protectors are immersed in freshly-mixed CPC-chitosan paste covered with a degradable mesh. Live cells, stained green, appear to have adhered and attained a normal polygonal morphology on all materials. Visual examination reveals that the density of live cells in each case is similar. Dead cells (stained red) are relatively few in all four cases. Therefore, the protectors are adequately protecting the cells from the setting of various compositions of freshly-mixed cement pastes.

FIG. 6(A): Scanning electron micrograph (SEM) showing cells attaching to CPC. "O" stands for osteoblasts. "E" designates the cytoplasmic extensions of the osteoblasts. FIG. 6(B): The tip of the cytoplasmic extension of the cell is attached to CPC. FIG. 6(C): Higher magnification showing the cytoplasmic extensions of the osteoblasts attaching to the hydroxyapatite crystals (HA) of CPC composite.

DESCRIPTION OF THE PREFERRED EMBODIMENTS

Figure 1:
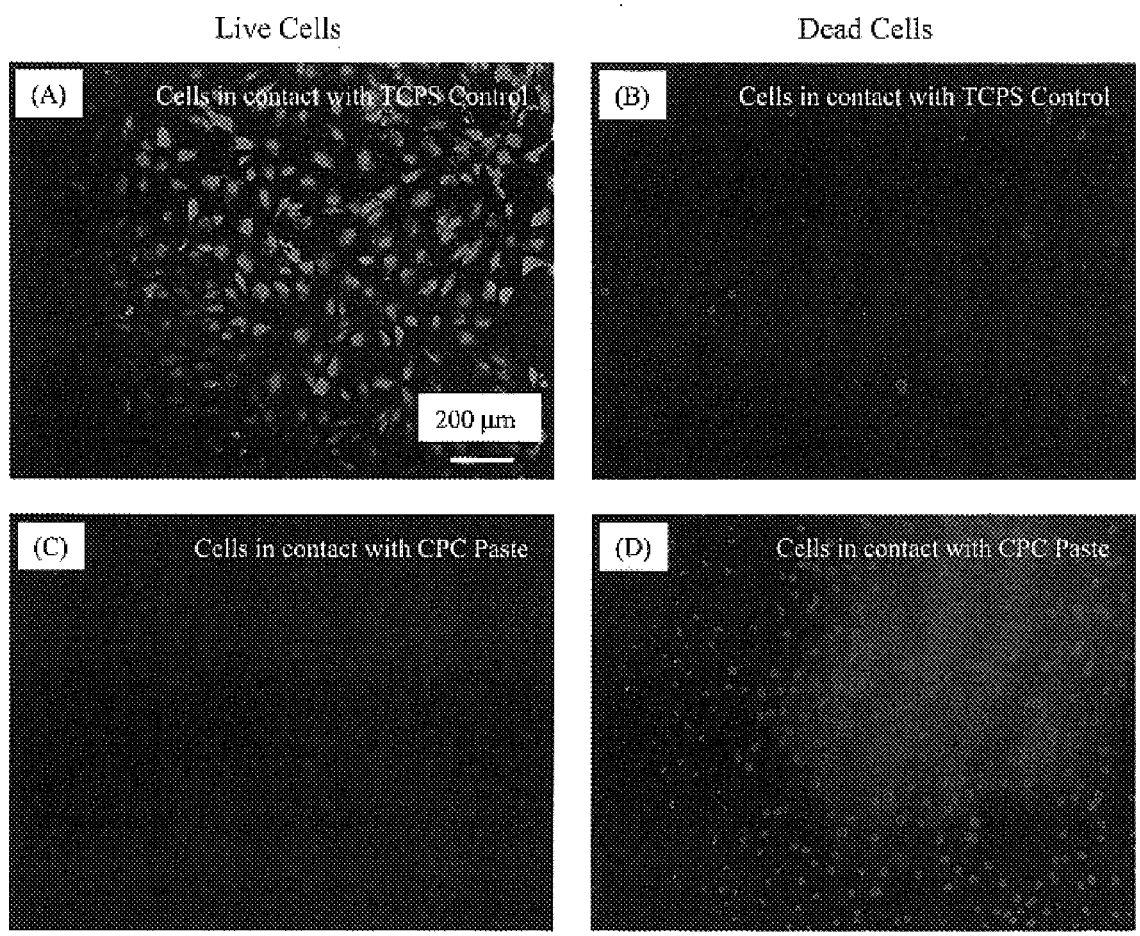
FIG. 1 is a series of enlarged photographs (FIGS. 1A, 1B, 1C, 1D) relating to experiments associated with the invention. Mouse osteoblast-like cells were cultured, and fifty thousand cells diluted into 2 mL of media added to each well of tissue culture polystyrene (TCPS). Freshly-mixed CPC paste is then placed into the wells; the other wells contain no CPC and serve as TCPS control. Cells of the control are mostly alive (stained green) with only a few dead cells (stained red). Cells in contact with the freshly-mixed CPC paste are nearly all dead. Hence cell protection is needed during the cement setting process. After CPC setting, cell protectors can then be dissolved to release the living cells inside the macropore structure of CPC created by the cell protector dissolution to grow new tissues.

The present invention relates to methods of surgical implant and tissue regenerating materials containing living cells useful for medical, veterinary, dental, craniofacial, and orthopedic repairs. This invention further relates to methods and compositions of engineered three-dimensional cell protectors inside a self-hardening implant matrix to protect the cells from any undesirable environment such as high or low pH, ion activities, mechanical disruption during mixing, placement and setting. Such cell protectors include three-dimensional lattice-like structures with cells living inside them, zigzag or woven or curved structures, or three-dimensional web-like structures. This invention further relates to methods and compositions for creating engineered three-dimensional pore architectures, at a prescribed time (for example, after matrix material setting), as cell activity passageways that are highly-interconnected throughout the entire implant. Still further, this invention relates to methods and compositions of surgical implants with three-dimensional cell protectors/pore architecture builders of designed sizes, effective diameters, interconnectivity sizes, and controlled degradation rates matching the applications, so that the cells can be released at a controlled time or at graded times after implant placement. Still further, this invention relates to methods and compositions of cell protectors having cells with different functions or different types of cells. Some cells are capable of generating new bone, while other cells can grow cartilage and blood vessels, still other cells can degrade or resorb the implant matrix. These different cells can be stored in different cell protectors, or be placed in different parts or layers inside the implant. These cell-containing protectors can be incorporated into an in-situ setting matrix, placed and set in a prepared tissue repair site. The protectors shield the cells from any harmful environmental effects of the chemistry or manipulation of the matrix for a prescribed time. Once it is safe for the cells, the protectors dissolve, release the cells, and concomitantly form three-dimensional pore architectures for biological functioning. Different cells can be released in different parts or locations of the implant. Different cells can also be released at different times, depending on the need and on the biocompatibility of the local environment. These locations and timings can be controlled by using different protectors and layered or graded structures.

The term "cell" refers to human and animal cells, including osteoblasts, osteoclasts and other bone cells, mesenchymal stem cells, fibroblasts; chondrocytes, odontoblasts, endothelial cells, and other progenitor cell lines.

The term "cell protector" refers to a structure, such as rods or tubes, with living cells inside to protect the cells from undesirable environments or contacts. The cell protector can also have three-dimensional lattice-like structures with cells living inside them, zigzag or woven or curved structures, spheres or blocks, random structures, or three-dimensional web-like structures.

The cell protector can be made from biocompatible and degradable or resorbable materials, including ceramics, polymers and composites. The diameter or thickness of the rod or tube of the cell protector ranges from 0.001 millimeter (mm) to 10 millimeter, preferably from 0.01 millimeter to 2 millimeter, most preferably from 0.1 millimeter to 1 millimeter (100 μm to 1000 μm).

The term "cell protector" and "pore architecture builder" refer to the same structure with two different functions: first protecting the living cells, then dissolving and building pore architectures for the cells to migrate and function in the implant. The pores have a similar structure as the cell protector, including rod or tube shapes, three-dimensional lattice-like structures, zigzag or woven or curved structures, spheres or blocks, random structures, or three-dimensional web-like structures.

The degradation rate for the cell protector would be for it to dissolve after surgical placement in the presence of biological fluids in a time period from 1 minute to three months, preferably from 1 hour to 3 weeks, most preferably from 4 hours to 1 week. The dissolution frees and releases the living cells spreading them throughout the entire implant to perform their biological function to resorb the matrix material and grow new tissues.

The term "degradation" and other similar terms, such as "dissolve", "soluble", "resorbable", "bioresorbing", and "biodegradable", describe materials that eventually disintegrate and dissolve in a certain environment, for example, bone graft materials in a physiological environment.

The following are illustrations of an example of a complete operational cycle of this invention. Other useful compositions and configurations will be within the scope of those skilled in the art.

An in-situ setting calcium phosphate matrix material, CPC, is used in this example. Tetracalcium phosphate (TTCP, $Ca_4[PO_4]_2O$) powder is mixed with dicalcium phosphate anhydrous (DCPA, $CaHPO_4$) powder to form the calcium phosphate cement powder. When mixed with a water-based liquid, the calcium phosphate cement sets to form solid hydroxyapatite. A biocompatible and degradable polymer is polymerized to form cell protectors: rods or tubes or a web-like structure (FIG. 1) with living cells inside each rod. These cell protectors are placed into the CPC paste, and then the cement paste is hardened. The cell protectors keep the cells from being harmed during the pH changes concomitant with the CPC setting and during mixing and manipulation of the cement during placement. Living cells mixed directly with the CPC paste without cell protectors died. Cells inside cell protectors are viable both before and after CPC setting. Once the CPC is set, it is biocompatible and not harmful to tile cells. Set CPC supports the cells. Therefore; the cell protectors are designed to dissolve after significant CPC setting, thus releasing the cells inside the set CPC to perform their biological function. Furthermore, the dissolution of the cell protector builds highly interconnected, tube-shaped or three-dimensional web-like pore structures for cell migration throughout the CPC to generate new tissue.

The present invention will be further understood in view of the following specific examples, which are merely illustrative and not meant to limit the scope of the invention.

EXAMPLE 1

An example of manufacture of this invention would be for medical, veterinary, dental, craniofacial and orthopedic bone repair. The CPC powder and liquid are mixed to form a paste that is filled into a stainless steel mold of 6 mm diameter and 3 mm depth. Distilled water is used as the cement liquid. Each specimen in the mold is sandwiched between two glass slides, and the assembly is incubated in a humidor with 100% relative humidity at 37° C. The hardening time is measured using a needle method with a load of 453.5 g and a flat tip diameter of 1.06 mm. A cement specimen is considered set when the needle loaded onto the specimen surface failed to leave a perceptible indentation. The time measured from the paste being mixed to this point is used as the setting time. Depending on composition and powder-to-water ratio, the setting time ranges from (14.5±1.3) min (82.8±4.4) min.

When the liquid contains water with sodium phosphate and hydroxypropyl methylcellulose, the cement setting time becomes (9.3±2.8) min. These setting times provide guidance on designing cell protectors with appropriate degradation rates.

EXAMPLE 2

An example of manufacture of this invention would be to incorporate living cells into a calcium phosphate cement for tissue repair. As an example, MC3T3-E1 osteoblast-like cells (Riken, Hirosaka, Japan) are cultured following established protocols (Simon et al., Preliminary report on the biocompatibility of a moldable, resorbable, composite bone graft consisting of calcium phosphate cement and poly(lactide-co-glycolide) microspheres. *J Orthop Res* 20:473-482, 2002; Xu et al., Self-hardening calcium phosphate composite scaffold for bone tissue engineering. *Journal of Orthopaedic Research* 22:535-543, 2004). Cells are cultured in flasks at 37° C. and 100% humidity with 5% CO2 (volume fraction) in a. modified Eagle's minimum essential medium (Biowhittaker, Walkersville, Md.). The medium is supplemented with 10% volume fraction of fetal bovine serum (Gibco, Rockville, Md.) and kanamycin sulfate (Sigma, St. Louis, Mo.), and changed twice weekly. Fifty thousand cells diluted into 2 mL of media are added to each well of tissue culture polystyrene (TCPS). Freshly mixed CPC paste is then placed into the wells; the other wells contain no CPC and serve as TCPS control. A fluorescence assay is used to assess the cellular viability of the cell populations from a visual perspective. Live cells display green fluorescence and dead cells display red fluorescence (Xu et al., Self-hardening calcium phosphate cement-mesh composite: Reinforcement, macropores, and cell response. *Journal of Biomedical Materials Research* 69A:267-278, 2004). FIG. 1 shows that the cells of the control are mostly alive (stained green) with only a few dead cells (stained red). In contrast, cells in contact with the freshly mixed CPC paste are nearly all dead. This experiment shows that although hardened CPC is known to be biocompatible, the CPC paste setting process can be harmful to the cells. Therefore, cell protection is needed during the setting process. After CPC setting, the cell protectors can be dissolved to release the cells inside CPC to perform their biological functions and grow tissues.

EXAMPLE 3

Figure 2:
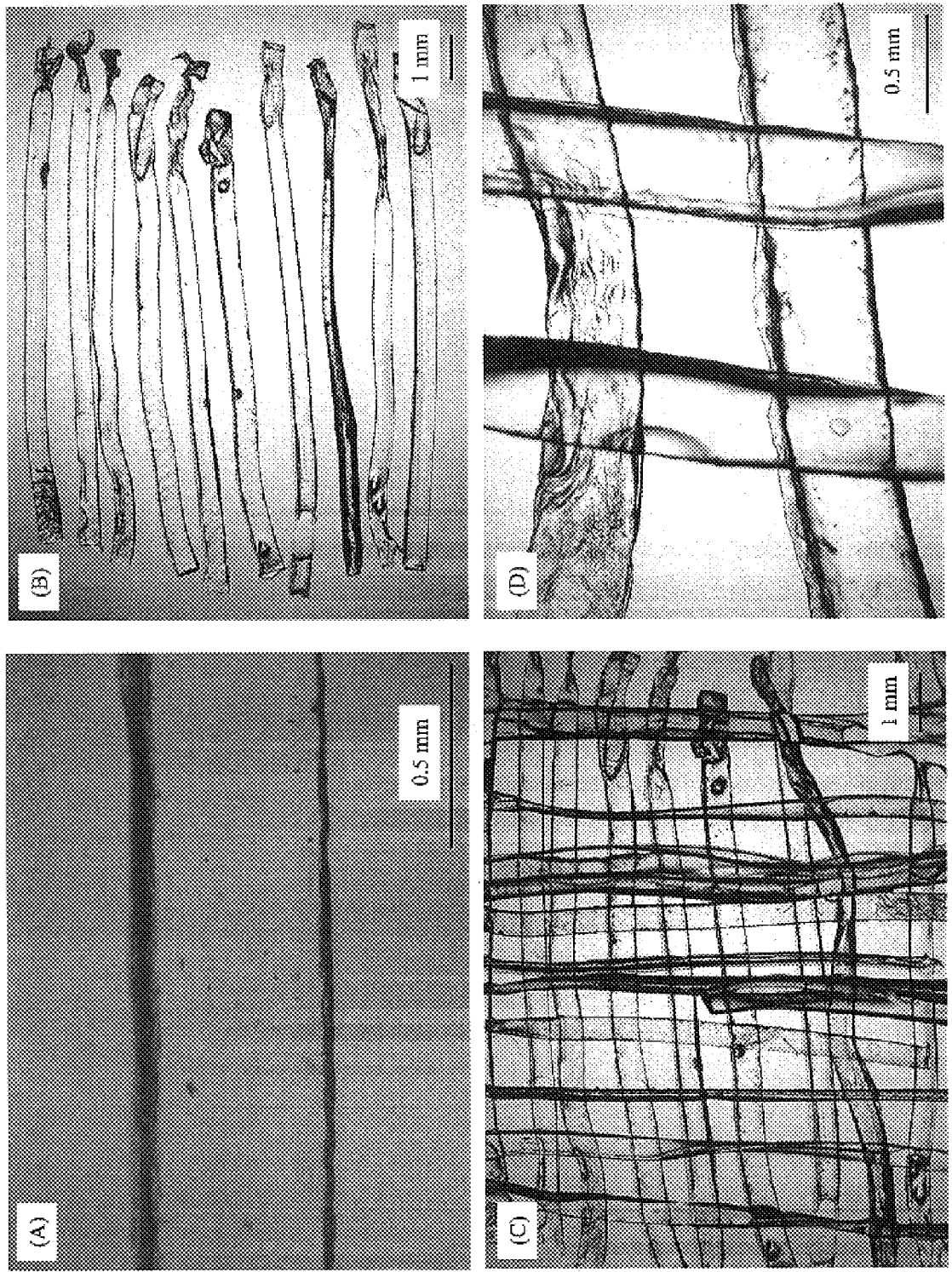
FIG. 2 is a series of photographs representing examples of the invention.

Another example of manufacture would be to produce in-situ setting CPC bone graft materials with living cells inside cell protectors that are mixed into the CPC paste. Biocompatible and degradable polymers, ceramics and composites can be used to construct the cell protectors. For example, a degradable polymer, poly(ethylene glycol)-anhydride dimethacrylate, is used as a rapidly degradable polymer for fabricating cell protectors. Structures such as those shown in FIG. 2 are fabricated by mixing osteoblast cells into the monomer liquid and then polymerizing the liquid into designed shapes inside molds. In the example in FIG. 2A, there are about 580 osteoblast cells inside each rod. These cell protector structures with living cells inside are mixed into the CPC paste, which is then mixed with an appropriate liquid and allowed to set to form an implant. The construct is immersed in water or in a physiological solution for the CPC to mature and for the cell protector to dissolve. It is measured that the cell protector dissolves in 506.5±50.3 min. This frees the cells and at the same time creates pore structures similar to the structures in FIG. 2, which are superior to conventional spherical or particle-shaped pores. The engineered three-dimensional tubular pore architecture thus designed facilitates cell migration, interaction, nutrient flow and generation of new tissues in the in vivo environment.

EXAMPLE 4

Another example of manufacture would be to produce in-situ setting materials that contain cell protectors having cells with different functions or different types of cells. For example, some cells are capable of generating new bone, while other cells can grow blood vessels, still other cells can degrade or resorb the CPC. Different cells can be stored in different protectors, or be placed in different parts or layers inside the implant. These cell-containing protectors can be incorporated into an in-situ setting paste, placed and set in a prepared tissue repair site. The protectors shield the cells from any harmful environment for a prescribed time. Once it is safe for the cells, the protectors dissolve and release the cells for biological functioning. Different cells can be released in different parts or locations of the implant. Different cells can also be released at different times, depending on the need and on the biocompatibility of the local environment. These locations and timings can be controlled by using different protectors and layered or graded structures.

EXAMPLE 5

Another example of manufacture of this invention would be to incorporate osteoblasts into a cell protector of a biocompatible polymer alginate, which then receive four different treatments: cells in protectors immersed in a cell culture medium; cells in protectors embedded in a CPC paste; cells in protectors embedded in a CPC-chitosan paste; and cells in protectors embedded in CPC-chitosan paste covered with a degradable mesh. Alginate is an alginic acid or a polysaccharide consisting of a copolymer of L-guluronic acid and D-mannuronic acid, and is biocompatible and degradable. The purpose of using chitosan is for strengthening. Chitosan (beta-(1,4)-2-amino-2-deoxy-D-glucose, or poly-D-glucosamine, or poly N-acetyl-D-glucosamine) and its derivatives are biocompatible and degradable. The purpose of using a degradable polymer mesh (polyglactin mesh, Ethicon, N.J.) is to further strengthen the implant. The purpose of this experiment is to examine whether the different CPC compositions would affect the cell viability inside the paste. Osteoblast cells are cultured in flasks at 37° C. and 100% humidity with 5% $CO_2$ (volume fraction) in a minimum essential cell medium. The medium is supplemented with 10% volume fraction of fetal bovine serum (Gibco, Rockville, Md.) and changed twice weekly, following established procedures (Simon et al., Preliminary report on the biocompatibility of a moldable, resorbable, composite bone graft consisting of calcium phosphate cement and poly(lactide-co-glycolide) microspheres. *J Orthop Res* 20:473-482, 2002; Xu et al., Self-hardening calcium phosphate cement-mesh composite: Reinforcement, macropores, and cell response. *Journal of Biomedical Materials Research* 69A:267-278, (2004).

Figure 3:
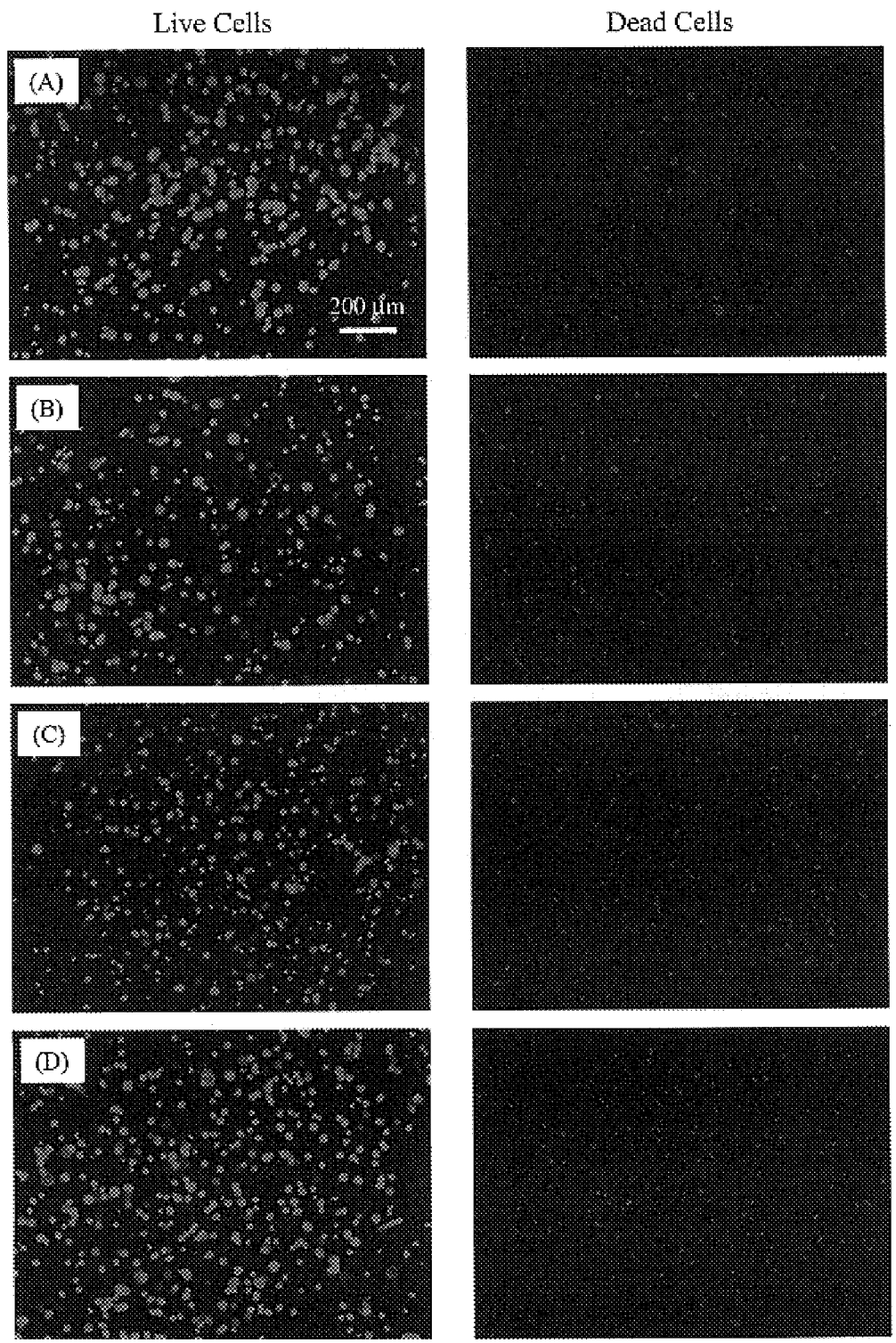
FIG. 3 is a series of photographs relating to the invention. Cells are cultured for 1 day with live cells staining green and dead cells staining red.

After 1 day of incubation of the cells inside the protectors receiving the above four treatments, the cells are then stained and viewed by epifluorescence microscopy (Eclipse TE300, Nikon, Melville, N.Y.). The results are shown in FIG. 3. Live cells (stained green) appear to have adhered and attained a normal, polygonal morphology. Visual examination reveals that the density of live cells is similar in all four treatments. Dead cells (stained red) are few and similar in all four treatments. This experiment shows that mixing the cell protectors into different CPC pastes does not harm the cells when compared to the control cells that are suspended in a cell culture medium only, and not mixed into a paste. This demonstrates that the cells are adequately protected from the manipulation and chemistry of the different matrix materials using this method. This is in direct contrast to the results in FIG. 1 without cell protectors.

EXAMPLE 6

Figure 4:
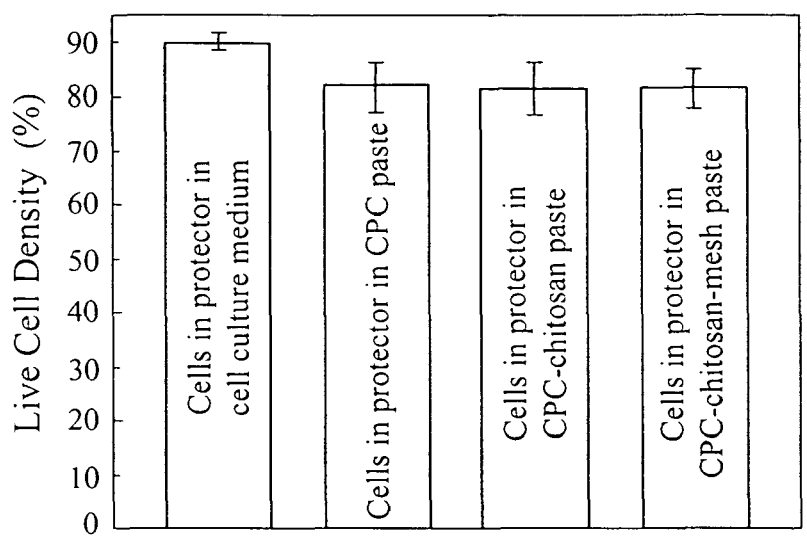
FIG. 4 is a chart or graph relating to experiments associated with the invention. Live cell density=number of live cells/(number of live cells+number of dead cells). Osteoblast cells are incubated inside protectors either immersed in a cell culture medium (control), embedded inside a CPC paste, inside a CPC-chitosan paste, or inside a CPC-chitosan-mesh paste. After 1 day of culture, the cells are stained and the numbers of live and dead cells are counted. Most of the cells are alive, indicating that the protectors are protecting cells from the harm of setting reactions of various cements.

Another example of manufacture of this invention would be to incorporate osteoblasts into a cell protector of a biocompatible polymer alginate, which then receives four different treatments: cells in protectors immersed in a cell culture medium; cells in protectors embedded in a CPC paste; cells in protectors embedded in a CPC-chitosan paste; and cells in protectors embedded in CPC-chitosan paste covered with a degradable mesh. The cells are cultured as described above. The numbers of live cells and dead cells are counted. Then the live cell density is calculated: Live cell density=number of live cells/(number of live cells+number of dead cells). The results are plotted in FIG. 4. The cells inside protectors embedded inside a CPC paste, a CPC-chitosan paste and a CPC-chitosan-mesh have similar live cell density values. These values are approaching the control with cell protectors immersed in the cell culture medium only without being embedded in a paste. This shows that the chemistry and manipulation of these various pastes do not harm the cells, and the cells are well protected inside the protectors.

EXAMPLE 7

Another example of manufacture of this invention would be to incorporate osteoblasts into a cell protector of a biocompatible polymer alginate, which then receive four different treatments: cells in protectors immersed in a cell culture medium; cells in protectors immersed in a CPC paste; cells in protectors immersed in a CPC-chitosan paste; and cells in protectors immersed in CPC-chitosan paste covered with a degradable mesh. A cellular assay, as described previously (Xu et al., Self-hardening calcium phosphate composite scaffold for bone tissue engineering. *Journal of Orthopaedic Research* 22:535-543, 2004), is used to quantify the cell viability. It measures the mitochondrial dehydrogenase activity which can be correlated to the cellular viability of the cells.

Figure 5:
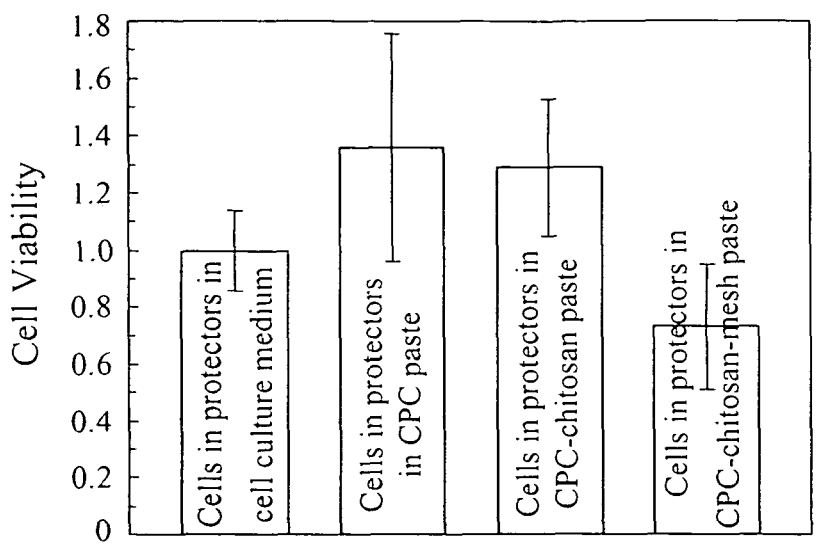
FIG. 5 is a chart or graph relating to cell viability. It shows the quantification of cell viability of osteoblast cells cultured for 1 day inside protectors either immersed in a cell culture medium (control), or embedded inside a freshly-mixed CPC paste, or inside a freshly-mixed CPC-chitosan paste, or inside a freshly-mixed CPC-chitosan-mesh paste. Cell viability of the three different compositions is not significantly different from that of the control in cell culture medium (Tukey's multiple comparison test; family confidence coefficient=0.95). This shows that the protectors are protecting the living cells from the harm of the setting reactions of various cement pastes.

After 14 days, the specimens with cells are transferred to wells in a 24-well plate and rinsed. Each reaction mixture is transferred to a 96-well plate and the absorbance is measured with a microplate reader. The results are shown in FIG. 5. The cells in protectors inside a CPC paste and inside a CPC-chitosan paste have viability values that are not significantly different from the control, which is immersed in only a cell culture medium. The cells in protectors inside CPC-chitosan-mesh have a lower viability than the other two pastes, but the cell viability is not statistically different from that of the cell culture medium control. These results show that embedding the cell protectors inside these three CPC pastes does not lower the cell viability, and the protectors are adequately protecting the cells.

EXAMPLE 8

Figure 6:
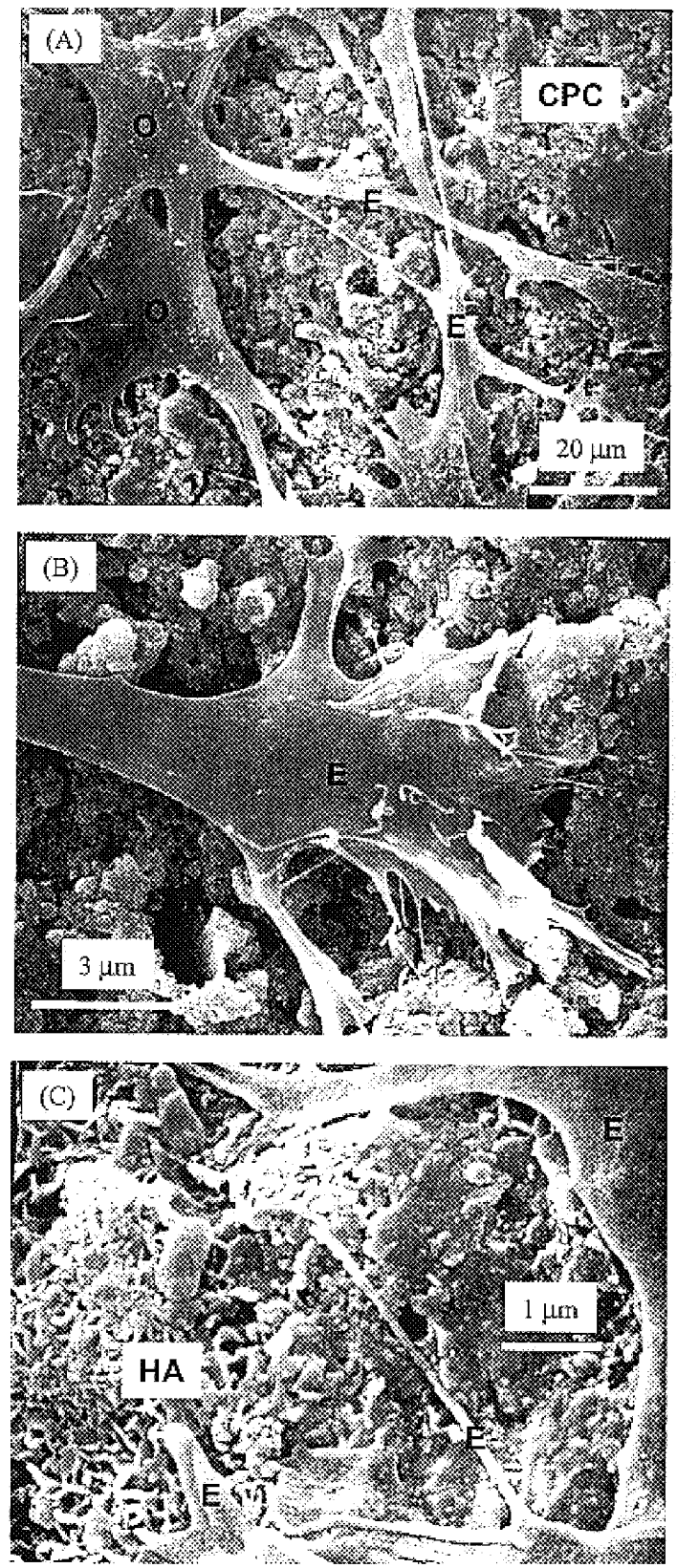
FIG. 6 is a series of SEMS.

Another example shows that once the CPC has set, it is biocompatible and does not harm the cells. Therefore, the cell protectors are only needed during CPC setting. After CPC setting, the protectors can dissolve away, thereby creating macropores for cell migration, cell-cell interaction, access to cell nutrients, and formation of new tissue inside the implant. A scanning electron microscope (SEM, JEOL 5300, Peabody, Mass.) is used to examine the set CPC specimens and the cells on the specimens. Cells cultured for 1 d on set hydroxyapatite cement specimens are sputter coated with gold and examined in the SEM. The results are shown in FIG. 6. The cells have displayed a healthy, normal, spread and polygonal morphology. The osteoblast cells ("O") have also developed cytoplasmic extensions ("E") that attach to the CPC surface and the hydroxyapatite ("HA") crystals in CPC composite. These cytoplasmic extensions are regions of the cell plasma membrane that contain a meshwork or bundles of actin-containing microfilaments which permit the movement of the migrating cells along a substratum. The cytoplasmic extensions are attached to the hydroxyapatite crystals in CPC. These results show that the set CPC is biocompatible and the cell protectors are only needed during CPC setting, thus allowing the cell protectors to fulfill their second function: dissolve away and build three-dimensional pore architectures throughout the CPC to allow cell functioning.

EXAMPLE 9

Another example of manufacture of this invention would be to produce implants that contain cells in protectors using different types of in-situ setting calcium phosphate materials. For example, dicalcium phosphate dihydrate (DCPD, $CaHPO_4.2H_2O$), a calcium phosphate compound known to possess a relatively high solubility and resorbability, can be used to replace the DCPA component in CPC. The high solubility of DCPD results in the fast setting of the cement, yielding a hardening time of about 15 min using water as the cement liquid and 6 min using a phosphate solution. Scanning electron microscopy reveals the progressive formation of nano-sized rod-like hydroxyapatite crystals and platelet crystals in the cements. The flexural strength quickly reaches 10.7 MPa for the DCPD cement containing degradable fibers in 30 minutes, compared to 0 MPa for the conventional CPC which does not set. Such a high early strength matches the reported strength for natural cancellous bone and sintered porous hydroxyapatite implants. The work-of-fracture (toughness) is increased by two orders of magnitude for the DCPD cement containing degradable fibers.

EXAMPLE 10

Another example of manufacture of this invention would be to produce in-situ setting CPC with cells and degradable fibers that has physical properties mimicking natural tissues. Osteoblast cells are contained inside polymer protectors in various shapes and structures, for example three-dimensional lattice-like structures, zigzag or woven or curved structures, spheres or blocks, or three-dimensional web-like structures. The protectors are then incorporated into the CPC paste. Degradable fibers, for example, degradable polymer fiber mesh (polyglactin mesh, Ethicon, N.J.), can be used in the surface layer of the CPC paste or in the prospective stress-bearing side of the implant. The paste containing osteoblast cells in protectors is set in 3 mm×4 mm×25 mm molds to fabricate flexural specimens. A three-point flexural test with a span of 20 mm is used to fracture the specimens at a cross head speed of 1 mm/min on a computer-controlled Universal Testing Machine (model 5500R, Instron Corp., Canton, Mass.). The specimen is loaded in flexure and the load-displacement curve is recorded by computer. The flexural strength is calculated by $S=3P_{max}L/(2bh^2)$, where $P_{max}$ is the maximum load on the load-displacement curve, L is flexure span, b is specimen width, and h is specimen thickness. Elastic modulus is calculated by $E=(P/d)(L^3/[4bh^3])$, where load P divided by the corresponding displacement d is the slope of the load-displacement (P–d) curve in the linear elastic region. Work-of-fracture, WOF, is calculated by $WOF=A(bh)$, where A is the area under the P–d curve, which is the work done by the load to deform and fracture the specimen.

Figure 7:
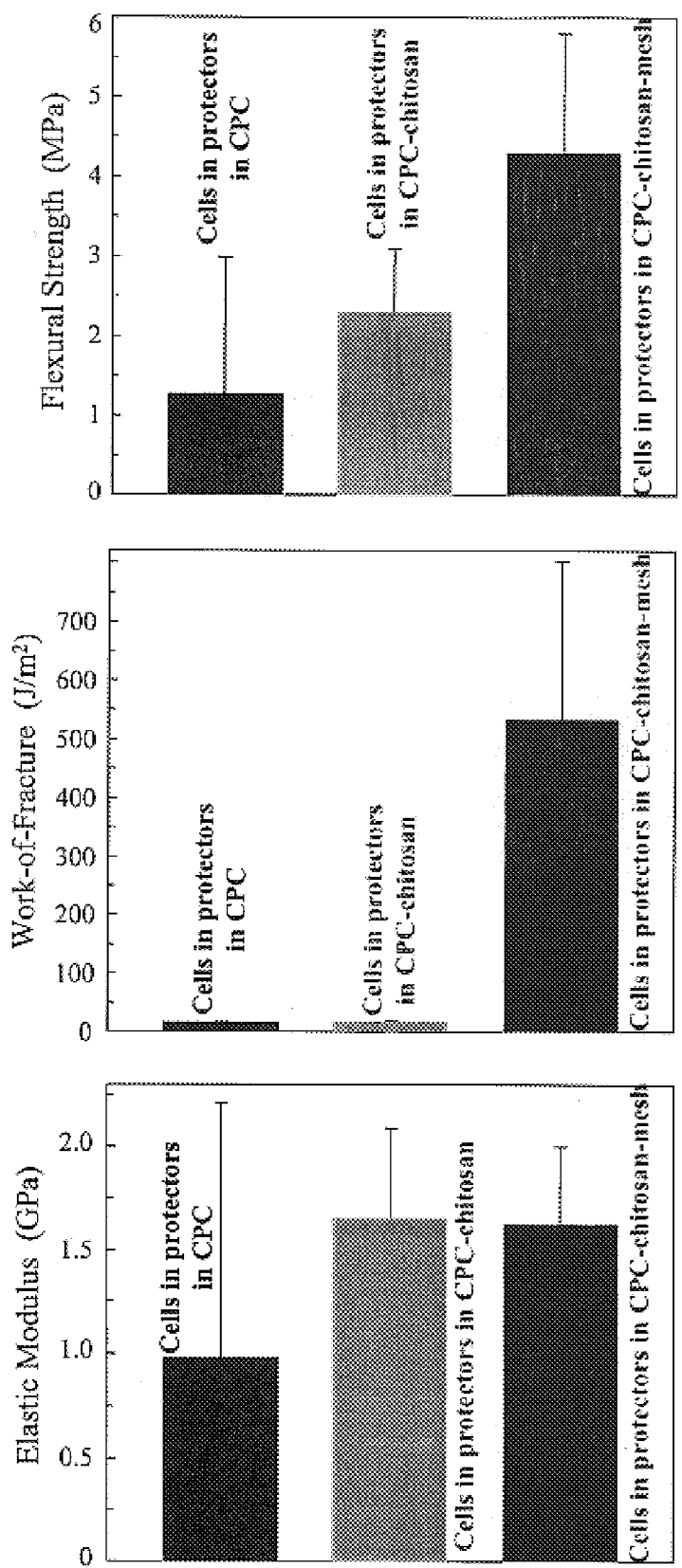
FIG. 7 is a series of charts or graphs relating to embodiments of the invention. Flexural strength of bar specimens of CPC containing living cells inside polymer protectors embedded inside three different CPC composites. Each value is the mean of six specimens with the error bar showing a standard deviation. Each CPC specimen of 3 mm×4 mm×25 mm has approximately 40% by volume of cell protectors. Each such specimen has approximately 12,150 osteoblast cells inside it.

The results are shown in FIG. 7 with specimens of CPC containing cells in protectors, CPC-chitosan containing cells in protectors, and CPC-chitosan-mesh containing cells in protectors. The CPC-chitosan-mesh material containing cells has a strength (mean±standard deviation, six repeats) of (4.3±1.5) MPa, an elastic modulus of (1.63±0.37) GPa, and a work-of-fracture (toughness) of (532±270) $J/m^2=$ (0.53±0.27) $kJ/m^2$. In this example, each specimen of 3 mm×4 mm×25 mm has approximately 40% by volume of cell protectors containing approximately 12,150 osteoblast cells.

EXAMPLE 11

Another example of manufacture of this invention would be to produce implant compositions containing living cells in protectors that are fabricated as pre-forms, which means that they are set in molds or machined to final shape and then used clinically. With pre-forms, pressure and other means can be used to control the material properties and porosity. Bone graft materials and implants with different shapes, sizes and layer structures can be produced as pre-forms. The pre-forms should be in contact with a cell medium to provide nutrients to the cells to maintain cell viability prior to implantation. Potential applications include mandibular and maxillary ridge augmentation, major reconstructions of the maxilla or mandible after trauma or tumor resection, dentine regeneration using odontoblast cells inside protectors, and other medical, veterinary, dental, periodontal, craniofacial and orthopedic applications.

EXAMPLE 12

Another example of manufacture of this invention would be to implant compositions containing living cells in protectors, and the cell protectors are made of degradable polymers with controlled dissolution rates to match applications.

The term "dissolution rate" here refers to the time it takes for the protector to disintegrate or dissolve when in contact with a water-containing solution. When immersed in a cell medium, it takes longer than a week before the alginate cell protectors disintegrate. Alginate is an alginic acid or a polysaccharide consisting of a copolymer of L-guluronic acid and D-mannuronic acid; it is a degradable and biocompatible polymer. It takes poly(ethylene glycol)-anhydride dimethacrylate cell protectors 8.4 hours to dissolve and free the cells. It takes gelatin cell protectors about 3 hours to dissolve and release the living cells. Gelatin is a complex combination of proteins obtained by hydrolysis of collagen, and is degradable and biocompatible.

This example illustrates the method to tailor and control the dissolution rates of cell protectors to match specific applications, for example to match the various setting times of calcium phosphate cements. Therefore, the cells will be protected from pH changes, ion activities and mechanical manipulation during cement placement and setting, then be promptly released from the protectors to fill the pore architectures thus created to initiate their biological activities and new tissue growth.

EXAMPLE 13

Figure 8:
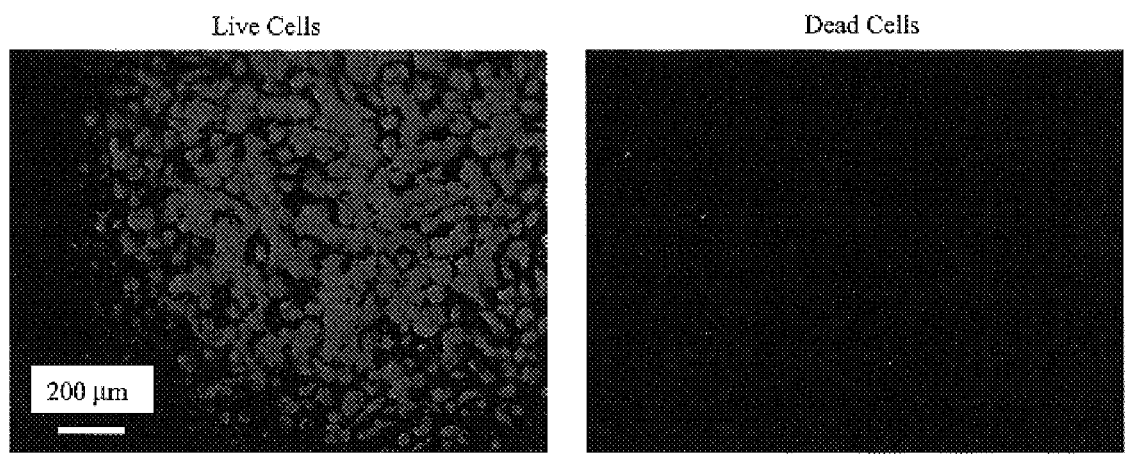
FIG. 8 is a collection of microphotographs associated with experiments relating to the invention. Cell protectors made of fast-degradable gelatin can dissolve in a few hours when immersed in a physiological solution. But it is important that the dissolution products of gelatin are not harmful to the cells. The photos show cells on TCPS in the presence of gelatin dissolution. After 24 hours with gelatin dissolution, live cells (stained green) are numerous and healthy. Dead cells (stained red) are very few. These results are similar to the control results using TCPS without the presence of gelatin, suggesting that the fast-dissolving gelatin containers do not harm the cells.

Another example of manufacture of this invention would be to implant compositions containing living cells in protectors, and the cell protectors are made of fast degradable gelatin. Cells can be placed into gelatin containers. These containers can then be incorporated into the CPC paste. After CPC setting, the gelatin containers dissolve away quickly (in a few hours) and free the cells in the CPC implant. Meanwhile, the dissolution of gelatin quickly creates pores for the cells to perform their biological functions and grow new tissues. However, it is critical that the dissolution products of the gelatin are not harmful to the cells. An experiment is performed in which the cells are seeded onto TCPS in the presence of gelatin containers to examine if the gelatin dissolution in the cell medium would harm the cells. After 24 hours with gelatin dissolution, live and dead staining of the cells is performed. The results are shown in FIG. 8. Live cells (stained green) appear to be numerous and healthy, while dead cells (stained red) are very few. These results are similar to results of control using TCPS without the presence of gelatin, suggesting that the fast-dissolving gelatin containers and their degradation products do not harm the cells.

EXAMPLE 14

Another example would be to match the mechanical strength and elastic modulus of the implant containing cell protectors with living cells to the strength and modulus of natural tissue being repaired, so that the CPC-cell construct can be used clinically without failing, fracture, or excessive deformation.

Natural cancellous bone has a reported tensile strength of about 3.5 MPa (Damien et al., Bone graft and bone graft substitutes: A review of current technology and applications. *J Appl Biomater* 2:187-208, 1991). Elastic modulus measured in flexure is about 12.8 GPa for natural cortical bone (Broz et al., Effects of deproteinization and ashing on site-specific properties of cortical bone. *J Mater Sci: Mater in Med* 8:395-401, 1997), and 0.3 GPa for cancellous bone (O'Kelly et al., A quantitative technique for comparing synthetic porous hydroxyapatite structure and cancellous bone. *J Mater Sci: Mater in Med* 7:207-213, 1996). Natural cortical bone has a work-of-fracture ranging from 0.4 to 1.5 kJ/m$^2$ (Lucksanasombool et al., Fracture toughness of bovine bone: influence of orientation and storage media. *Biomaterials* 22:3127-3132, 2001).

Other studies have also developed biomaterials with living cells inside. A strength of about 0.06 MPa is reported (Drury et al., The tensile properties of alginate hydrogels. *Biomaterials* 25:3187-3199, 2004). An elastic modulus of about 18 kPa=0.018 MPa=0.000018 GPa is measured (Lee et al., Degradable and injectable poly(aldehyde guluronate) hydrogels for bone tissue engineering. *J Biomed Mater Res* 56:228-233, 2001). These values are lower than the respective values for natural bone by more than an order of magnitude.

Other stronger biomaterials are available, but the strong biomaterials do not have the ability to contain living cells prior to placement. They may not be bioactive, or are not degradable.

This discovery, for example, the CPC-chitosan-mesh containing cells in protectors with 12,150 osteoblast cells in a specimen of 3 mm×4 mm×25 mm, possesses a flexural strength (mean±standard deviation; 6 repeats) of (4.3±1.5) MPa. This matches the 3.5 MPa for natural cancellous bone, and exceeds the 0.06 MPa value previously reported for the other biomaterial cited above.

Our in-situ setting material with 12,150 osteoblast cells in a specimen of 3 mm×4 mm×25 mm has an elastic modulus of (1.63±0.37) GPa. This is in between the 0.3 GPa for natural cancellous bone and 12.8 GPa for natural cortical bone, and exceeds the previously reported value of 0.000018 GPa for the biomaterial cited above.

Our implant material containing 12,150 osteoblast cells in a specimen of 3 mm×4 mm×25 mm possesses a work-of-fracture value of 0.53 kJ/m$^2$, similar to 0.4 to 1.5 kJ/m$^2$ reported for natural cortical bone.

Based on our literature search, our self-hardening implant material is the only reported material that: (i) contains living cells prior to placement and hardening; (ii) can be molded or injected to intimately fit the tissue cavity; (iii) contains cell protectors that can build three-dimensional pore architectures filled with cells throughout the implant; and (iv) possesses mechanical strength, elastic modulus and work-of-fracture values that match the values of natural cancellous bone or cortical bone.

Such matching has critical biomimetic importance. The term "Biomimetic" here refers to the imitation, simulation or reproduction of biological natural materials. For example, if an artificial bone repair material has an elastic modulus much higher than the modulus of natural bone, it can cause stress shielding and bone resorption. If the artificial material has too low a strength or toughness compared to natural bone, the implant or bone graft may be damaged or fail catastrophically in use.

EXAMPLE 15

Another example of manufacture of this invention would be for medical, dental, craniofacial and orthopedic bone repair. Tissue generating cells are obtained from the patient, and then multiplied in the laboratory. The cells are suspended in a solution. The solution is poured into a mold of a tubular shape. The solution containing the cells is then hardened or gelled by chemical reaction or light activation to form fibers, rods or tubes containing cells. The fibers, rods or tubes are then cut to fragments, mixed into a CPC paste, and placed into the prepared bone site or cavity of the patient. The fragments protect the cells during paste mixing, placement, and paste setting. After that, the fragments dissolve, releasing the cells throughout the CPC implant. Furthermore, the dissolution of the fragments creates long pores in CPC for the cells to migrate, interact and make new tissue.

The thickness of the rod or tube or fiber of the cell protector ranges from 0.001 mm to 10 mm, preferably from 0.01 mm to 2 mm, most preferably from 0.1 mm to 1 mm (100 µm to 1000 µm, 1 µm=$10^{-6}$ meter=$10^{-3}$ mm). The length of the rod, fiber or tube fragment ranges from 1 meter to 10 µm, preferably from 100 mm to 100 µm, most preferably from 10 mm to 1 mm.

EXAMPLE 16

Another example of manufacture of this invention would be for medical, dental, craniofacial and orthopedic bone repair using injectable CPC paste containing tubes or fibers or rods filled with cells. Injectable pastes are less dry and more effective to fill bone defects with irregular shapes and corners. The injection technique is also location-accurate and minimally invasive. The paste can be injected through a medical syringe. An opening of 2 mm inner diameter can be used for the syringe tip. The CPC paste is filled into the syringe, and a force is applied to the syringe plunger to push the paste out through the tip into a bone cavity. The rods or tubes or fibers in the CPC paste can be fabricated as described in the preceding example filled with cells from the patient. Alternatively, one or several long tubes that are soft or flexible can be continuously injected out with the flowing CPC paste into the prepared bone site. The long tubes or rods filled with cells can have a length ranging from 3 mm to 100 mm, preferably from 10 mm to 30 mm. The syringe tip opening can vary from 0.5 mm to 10 mm depending on the bone cavity size, preferably from 1 mm to 5 mm.

EXAMPLE 17

Another example of manufacture of this invention would be for medical, dental, craniofacial and orthopedic bone repair using inserts filled with cells that can be inserted into a CPC paste inside the bone cavity. Tissue generating cells are obtained from the patient, and then multiplied in the laboratory. The cells are suspended in a solution. The solution is poured into a mold to make an insert. An insert is a relatively large filler. A filler is an object that can be filled or pushed into a CPC paste. The solution containing the cells in the insert mold is then hardened or gelled by chemical reaction or light activation to form an insert. The insert can be in the shape of a single elongated object, or several rods connected into a three-dimensional structure, depending on the mold design and clinical needs. The CPC paste is poured into the bone cavity. Then the insert is inserted or pushed into the CPC paste. The insert could also be placed into the bone cavity followed by being infiltrated by the CPC paste. The insert protects the cells inside it from the force of pushing, as well as from the CPC setting reaction. After that; the insert is dissolved, releasing the cells inside the CPC implant. Furthermore, the dissolution of the insert creates a macropore or a three-dimensional pore structure for the cells to migrate, interact and make new tissue inside the CPC implant.

The insert can have a diameter ranging from 0.5 mm to 10 mm, and a length of 1 mm to 50 mm. In the case of a three-dimensional insert, it can have a size ranging from 0.1 mm to 50 mm, preferably from 3 mm to 10 mm. Either one insert can be pushed into the CPC paste, or several inserts can be pushed in together. The insert can have a size much smaller than the bone cavity size, or a size similar to the bone cavity size. For example, if the bone cavity and the CPC paste is 10 mm deep, the insert can have a 10 mm height. Therefore, the two ends of the insert are exposed and not buried inside the CPC. After the insert dissolves, the pore structure is exposed to the body fluid and biological agents in the bone to help the cells make new tissue in the CPC implant.

The implant material of the invention as elucidated by the examples may have a broad range of features. The "cell protectors" are three-dimensional cavity structures which in a preferred embodiment are interconnected throughout a matrix material. The cavities are preferably interconnected and can serve therefore as passageways providing for nutrient transfer, cell migration through the implant and tissue growth into the implant. The matrix material may be any one of a number of materials and preferred embodiments including the following:

(a) Tetracalcium phosphate ($Ca_4[PO_4]_2O$, TTCP) based self-hardening calcium phosphate cements (for example, mixtures of TTCP with dicalcium phosphate anhydrous DCPA, or $CaHPO_4$);

(b) alpha-tricalcium phosphate (alpha-TCP, $\alpha$-$Ca_3[PO_4]_2$) based self-hardening calcium phosphate cements (for example, mixtures of alpha-TCP with calcium carbonate, $CaCO_3$);

(c) beta-tricalcium phosphate (beta-TCP, $\beta$-$Ca_3[PO_4]_2$) based self-hardening calcium phosphate cements (for example, mixtures of beta-TCP with hydroxyapatite, $Ca_5[PO_4]_3OH$);

(d) DCPA-based or dicalcium phosphate dihydrate (DCPD, $CaHPO_4.2H_2O$) based self-hardening calcium phosphate materials, for example, mixtures of DCPA with calcium hydroxide, $Ca(OH)2$;

(e) amorphous calcium phosphate-based self-hardening calcium phosphate materials. (The term amorphous refers to the material being not crystalline or being poorly crystalline.)

(f) calcium phosphate-polymer composite materials including non-rigid or elastomeric agents, for example, chitosan and its derivatives, gelling agents, for example, hydroxypropl methylcellulose, carboxyl methylcellulose, starch, proteoglycans, and glycoproteins.

The cells may be grown in vitro as well as in vivo. Because of the cell protector structure, the implant material, when immersed in a cell culture solution or in vivo, serve as passageways for nutrient transfer and successful tissue growth from the cells retained within the cell protector units. Many types of materials may be utilized to function as a cell protector from biodegradable, biocompatible and resorbable materials and further including materials which are not necessarily degradable. Biocompatibility, of course, is preferred. Such materials include ceramics, glasses, polymers and organic materials, inorganic materials and mixtures thereof.

Preferably, the cell protectors have a three-dimensional characteristic. That is, they are arrayed throughout the matrix material. However, it is possible to provide for structures wherein the cell protectors are arranged in desired patterns so as to provide for desirable patterns of growth of the cells in vivo. The matrix material is preferably one that will set and self harden.

Traditionally nutrients that should be included inside cell protectors are: cell culture medium containing the appropriate concentration of inorganic salts, amino acids and vitamins (as prescribed by the Tissue Culture Association). Additionally, this is supplemented with antibiotics such as kanamycin or penicillin/streptomycin to prevent infection, glutamine and sodium private to enhance the synthesis of nucleic acids and serum, which provides proteins essential for the attachment, proliferation and sustainability of cell protector systems in vitro.

The integration of nutrients and biological factors that provide a positive stimulus for cells is important when designing biomaterials in general and a cell protector system in particular. These factors can be divided into two groups: 1.) soluble factors that are incorporated as a mixture with traditional cell culture medium inside the cell protector, and 2.) factors that are incorporated directly into the matrix of the cell protector by physical and/or chemical methods.

The first group consists of traditional protector matrices that encapsulate cells that are suspended in an aqueous medium. This medium contains chemically defined components that provide nutrients for cell culture growth such as inorganic salts, sugars, amino acids and vitamins. This is supplemented with antibiotics such as kanamycin or penicillin/streptomycin to prevent infection, glutamine and sodium private to enhance the synthesis of nucleic acids and serum, which provides proteins essential for the attachment, proliferation and sustainability of cell protector systems in vitro. Additional factors may be included which elicit a more direct cellular response such as extracellular matrix production, proliferation, differentiation and migration, to name only a few. These factors primarily include growth factors such as transforming growth factor β (TGF-β), fibroblast growth factor (FGF) vascular endothelial growth factor (VEGF), and bone morphogenic proteins (BMPs), and extracellular matrix proteins such as fibronectin.

The second group consists of cell protector matrices that are both naturally occurring and inherently bioactive themselves or are materials (synthetic or natural) that are chemically or physically modified to provoke a specific cellular response. Collagen gels can be created that provide both a protective environment for cells and an environment that closely resembles that of the extracellular matrix in vivo. In order to impart bioactivity on biologically inert materials, bioactive molecules such as fibronectin and growth factors can be physically bound to the surface of the material. Additionally, specific peptide sequences can be grafted onto the surface of materials such as the polysaccharides hyaluronic acid or alginate and synthetic polymer networks like poly(ethylene glycol)-based hydrogels or poly(hydroxyethyl) methacrylate hydrogels to create specific cell responses such as a modulation of inflammatory response, attachment, migration and differentiation.

The cell material is human or animal cells, including but not limited to osteoblast, osteoclasts, other bone cells, mesenchymal stem cells, fibroplasts, chondrocytes, odontoblasts, endothelial cells and other progenitor cells and stem cells.

The general size and configuration of the cell protector is varied. For example, the diameter or thickness of a rod or tube comprising a cell protector may range from 0.001 mm to 10 mm. Preferably, the size range is 0.01 mm to 2 mm and most preferably in the range of 0.1 mm to 1 mm.

While there has been set forth various examples and embodiments of the invention, it is to be understood that the invention is limited only by the following claims and equivalents thereof.

What is claimed is:

1. A moldable implant material for implantation of living cells, comprising:
   (a) at least one living cell;
   (b) a cell protector material, characterized in that the cell protector material is biocompatible with said at least one living cell, biodegradable in situ subsequent to implantation,-in the form of rods or tubes having a diameter in the range of about 0.001 mm to 10 mm and a length in the range of about 10 mm to 1 mm, and the rods or tubes interconnect to form a three-dimensional, interconnected structure; and
   (c) a matrix material, characterized in that the matrix material is, at least in part, biocompatible in vivo, hardenable in situ subsequent to implantation, and comprises a calcium and phosphorous compound selected from the group consisting of tetracalcium phosphate ($Ca_4[PO_4]_2$ O, TTCP) based self-hardening calcium phosphate cements, alpha-tricalcium phosphate (alpha-TCP, $\alpha$-$Ca_3[PO_4]_2$) based self-hardening calcium phosphate cements, beta-tricalcium phosphate (beta-TCP, $\beta$-$Ca_3[PO_4]_2$) based self-hardening calcium phosphate cements, dicalcium phosphate anhydrous (DCPA, $CaHPO_4$) based self-hardening calcium phosphate cements, dicalcium phosphate dihydrate (DCPD, $CaHPO_4 \cdot 2H_2O$) based self-hardening calcium phosphate materials, amorphous calcium phosphate-based self-hardening, calcium phosphate materials, and combinations thereof;
   wherein the cell protector material substantially encapsulates the at least one living cell; and
   wherein the cell protector material, comprising the at least one living cell, is contained, at least in part, within the matrix material.

2. The moldable implant material of claim 1, wherein the matrix material is, at least in part, biodegradable.

3. The moldable implant material of claim 2, wherein the cell protector material has a faster biodegradation rate in situ than the matrix material.

4. The moldable implant material of claim 1, wherein the at least one living cell is selected from the group consisting of osteoblasts, osteoclasts, bone cells, mesenchyinal stem cells, fibroblasts, chondrocytes, odontoblasts, endothelial cells, progenitor cells, stem cells, and combinations thereof.

5. The moldable implant material of claim 1 wherein the at least one living cell is selected from the group consisting of bone cells and progenitors of bone cells.

6. The moldable implant material of claim 1, wherein the cell protector material comprises a material selected from the group consisting of biodegradable or resorbable ceramics, organic materials, inorganic materials, and combinations thereof.

7. The moldable implant material of claim 6, wherein the cell protector material comprises an organic Material.

8. The moldable implant material of claim 1 wherein the cell protector material comprises about 5% to about 95% by volume of the implant material.

9. The moldable implant material of claim 1 wherein the cell protector material comprises about 20% to about 80% by volume of the implant material 10. The moldable implant material of claim 1 wherein the cell protector material comprises about 30% to about 70% by volume of the implant material 11. The moldable implant material of claim 1, wherein the matrix material comprises two species of calcium and phosphorous compounds selected from the group consisting of tetracalcium phosphate ($Ca_4[PO_4]_2O$, TTCP) based self hardening calcium phosphate cements, alpha-tricalcium phosphate (alpha-TCP, $\alpha$-$Ca_3[PO_4]_2$) based self hardening calcium phosphate cements, beta-tricalcium phosphate (beta-TCP, $\beta$-$Ca_3[PO_4]_2$) based self hardening calcium phosphate cements, dicalcium phosphate anhydrous (DCPA, $CaHPO_4$) based self hardening calcium phosphate cements, dicalcium phosphate dihydrate (DCPD, CaHPO$_4$ ·2H$_2$O) based self hardening calcium phosphate materials, amorphous calcium phosphate-based self-hardening, calcium phosphate materials, and combinations thereof.

12. The moldable implant material of claim 1, wherein the matrix material is comprised of a carrier material which is hardenable in situ subsequent to implantation.

13. The moldable implant material of claim 1 wherein the matrix material is, at least in part, not biodegradable.

14. The moldable implant material of claim 1, further comprising (d) a cell nutrient material.

15. The moldable implant material of claim 1, wherein the implant material is in the form of a plastic paste.

* * * * *